United States Patent [19]

Crayton et al.

[11] Patent Number: 5,608,316

[45] Date of Patent: Mar. 4, 1997

[54] APPARATUS FOR DETECTING PARTICLES IN A FLUID AND A METHOD FOR OPERATING SAME

[75] Inventors: John W. Crayton, Washington; John J. Krone, Dunlap; Terry D. Oltman, Chillicothe; Cecilia A. Walacavage, East Peoria, all of Ill.

[73] Assignee: Caterpillar Inc., Peoria, Ill.

[21] Appl. No.: 518,478

[22] Filed: Aug. 21, 1995

[51] Int. Cl.⁶ .......................... G01N 27/74; G01R 33/12
[52] U.S. Cl. .................. 324/204; 324/225; 324/232; 324/236; 340/631
[58] Field of Search .................... 324/204, 225, 324/232, 234, 236; 340/631; 73/61.42; 210/85

[56] References Cited

U.S. PATENT DOCUMENTS

| | | | |
|---|---|---|---|
| 2,671,200 | 3/1954 | Lederer | 324/71 |
| 3,748,576 | 7/1973 | Sigournay | 324/41 |
| 3,878,103 | 4/1975 | Miller et al. | 210/243 |
| 4,004,216 | 1/1977 | Natens et al. | 324/41 |
| 4,059,795 | 11/1977 | Mordwinkin | 324/233 |
| 4,176,545 | 12/1979 | Oddo | 73/64 |
| 4,219,805 | 8/1980 | Magee et al. | 340/631 |
| 4,523,146 | 6/1985 | Champaigne | 324/204 |
| 4,536,713 | 8/1985 | Davis et al. | 324/324 |
| 4,553,094 | 11/1985 | Gehrke | 324/225 |
| 4,563,644 | 1/1986 | Lenander et al. | 324/232 |
| 4,651,091 | 3/1987 | Chambers et al. | 324/204 |
| 4,651,092 | 3/1987 | Brunsch et al. | 324/204 |
| 4,731,578 | 3/1988 | Tsaprazis | 324/204 |
| 4,766,373 | 8/1988 | Chambers et al. | 324/204 |
| 4,831,362 | 5/1989 | Tsaprazis | 340/515 |
| 4,837,511 | 6/1989 | Whittington et al. | 324/236 |
| 4,841,244 | 6/1989 | Chambers | 324/204 |
| 4,878,019 | 10/1989 | Tsaprazis et al. | 324/204 |
| 4,893,079 | 1/1990 | Kustra et al. | 324/234 X |
| 4,926,120 | 5/1990 | Veronesi et al. | 324/204 |
| 5,001,424 | 3/1991 | Kellett et al. | 324/204 |
| 5,027,065 | 6/1991 | Bares et al. | 324/204 |
| 5,061,364 | 10/1991 | Metala et al. | 210/85 |
| 5,118,410 | 6/1992 | Rumberger | 210/85 |
| 5,334,932 | 8/1994 | Nielsen | 324/204 |
| 5,388,448 | 2/1995 | Showalter et al. | 73/61.71 |
| 5,444,367 | 8/1995 | Kempster et al. | 324/225 X |

FOREIGN PATENT DOCUMENTS

| | | | |
|---|---|---|---|
| 2101330 | 1/1983 | United Kingdom | 324/204 |
| 2132358 | 7/1984 | United Kingdom | |

*Primary Examiner*—Gerard R. Strecker
*Attorney, Agent, or Firm*—David M. Masterson; Mario J. Donato

[57] ABSTRACT

In one aspect of the present invention, an apparatus for detecting particles within a fluid is disclosed. A bobbin defines a debris collection chamber. A first coil is wound in a helix about the bobbin in the proximity of the debris collection chamber, wherein the induction of the first coil is responsive to the particle accumulation within the collection chamber. A reference coil is wound in a helix about the bobbin to compensate for changing fluid temperature. An oscillator is coupled to the first and reference coils for selectively energizing the coils with an oscillating waveform at a frequency that induces eddy currents in the particles. The frequency of the oscillating waveform is indicative of the amount of accumulation of both the ferrous and nonferrous particles.

19 Claims, 4 Drawing Sheets

Fig_1_

Fig_2_

APPARATUS FOR DETECTING PARTICLES IN A FLUID AND A METHOD FOR OPERATING SAME

TECHNICAL FIELD

This invention relates generally to an element in a fluid system, and more particularly, to a device for detecting ferrous and nonferrous metallic particles in a fluid.

BACKGROUND ART

Hydraulic systems are important to many work machines and represent large expenses in the event of component failure. If failures are detected early, repair expenses can be minimized; however, if catastrophic failure occurs, the large amounts of particles caused by the failure can enter the hydraulic system and cause damage to many other components. Fortunately, any catastrophic failure of one of the components is often preceded by the gradual breakup of one or more components. This break-up can be detected so that corrective action can be taken before any further damage to surrounding components occurs.

In the past, there have been several different ways to detect metallic particles within a fluid. One such system is described by Magee et al. in U.S. Pat. No. 4,219,805. This system captures ferrous particles that are contained in a fluid medium, and indicates the mass of any significant individual ferrous particles and the total mass of such particles that have accumulated over a predetermined time period. However, this system is limited to the detection of ferrous particles, e.g., iron; as opposed to non-ferrous particles, e.g., copper, brass, or nonmagnetic stainless steel.

The present invention is directed to overcoming one or more of the problems set forth above.

DISCLOSURE OF THE INVENTION

In one aspect of the present invention, an apparatus for detecting particles within a fluid is disclosed. A bobbin defines a debris collection chamber. A first coil is wound in a helix about the bobbin in the proximity of the debris collection chamber, wherein the induction of the first coil is responsive to the particle accumulation within the collection chamber. A reference coil is wound in a helix about the bobbin to compensate for the changing temperature of the fluid. An oscillator is coupled to the first and reference coils for selectively energizing the coils with an oscillating waveform at a frequency that induces eddy currents in the particles. The frequency of the oscillating waveform is indicative of the amount of accumulation of both the ferrous and non-ferrous particles.

BRIEF DESCRIPTION OF THE DRAWINGS

For a better understanding of the present invention, reference may be made to the accompanying drawings in which.

BEST MODE FOR CARRYING OUT THE INVENTION

Figure 1:
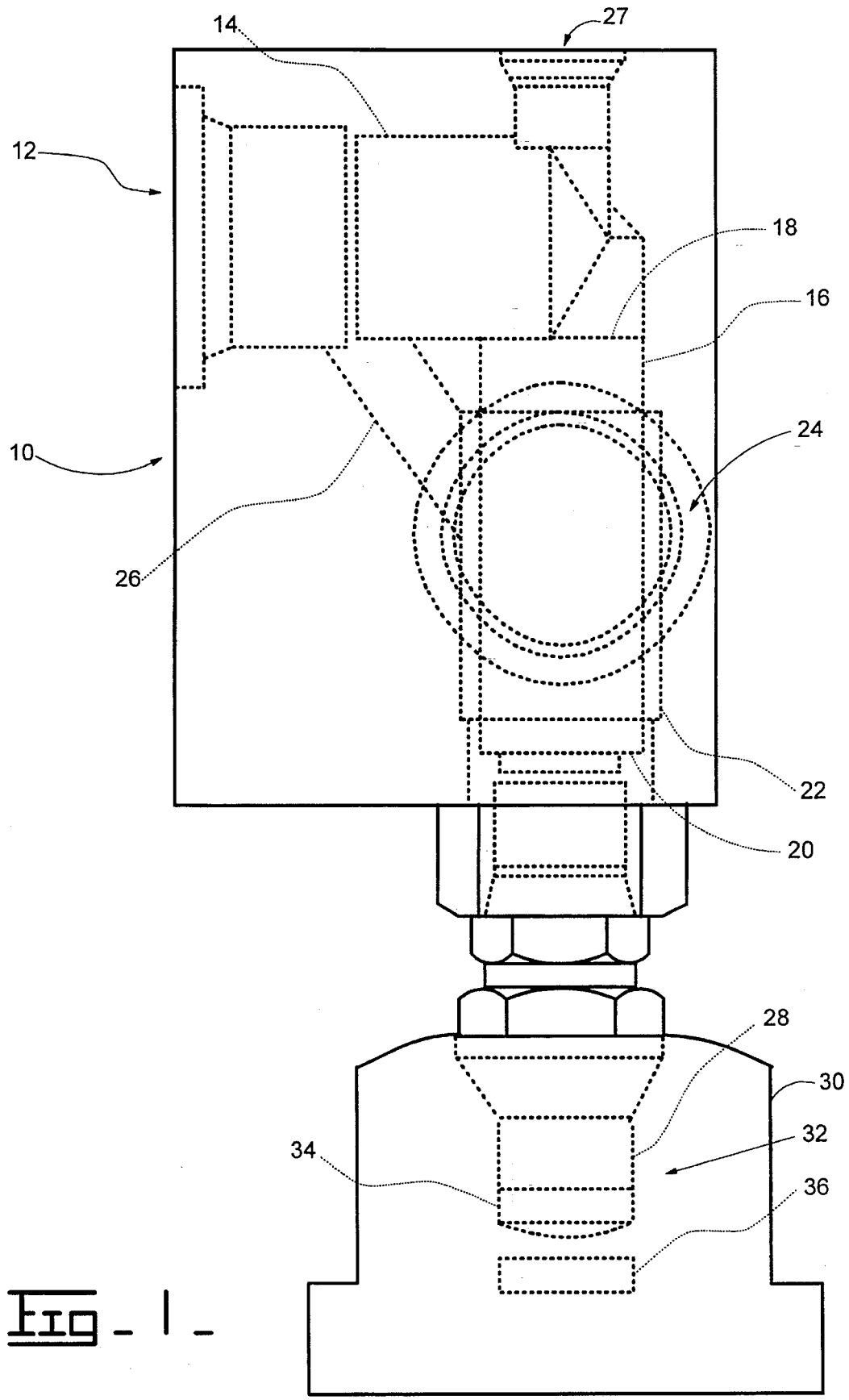
FIG. 1 is a diagrammatic view of a housing that includes an apparatus for filtering debris in a fluid and an apparatus for sensing such debris.

Referring to FIG. 1, an apparatus for filtering debris from a fluid and indicating the accumulation of the debris is referred to generally by the reference 10. An inlet port 12 is adapted for connection to a hydraulic fluid line and directs fluid to an inlet chamber 14. The inlet chamber 14 is cylindrical in shape and is preferably disposed at substantially a right angle to a screen 16. It should be understood, however, that the precise angular relationship of the inlet chamber 14 and screen 16 is not critical.

In the preferred embodiment, the screen 16 is cylindrical in shape and of approximately the same diameter as the inlet chamber 14. Advantageously, the screen 18 is formed of stainless steel "40" mesh and is open on each end 18,20 of the cylinder formed by the screen 18. While this particular screen is not required, the screen is advantageously made of non-magnetic material and has a mesh size small enough to catch most particles while not significantly restricting flow. Fluid flows freely from the inlet chamber 14 downwardly into the cylinder defined by the screen 16 through the top opening 18. The screen 16 preferably extends coaxially in a screen chamber 22 of slightly larger diameter than the screen 16.

As is appreciated by those skilled in the art, the amount that the screen chamber 22 is larger than the screen 16 must be sufficient to not restrict the flow of fluid. The screen chamber 22 is connected to an outlet port 24 that allows fluid flowing out of the screen 16 into the screen chamber 22 to exit the apparatus 10. Thus, the fluid entering the top of the cylinder defined by the screen 16 is filtered as it passes radially outwardly through the screen 16 into the screen chamber 22. The filtered fluid then exits the apparatus 10 via the outlet port 24.

A bypass port 26 extends between the inlet port and chamber 12,14 and the screen chamber 22. As shown, the bypass port 26 preferably extends downwardly and radially inwardly toward the screen 16. By virtue of this arrangement, fluid flows in a direction counter to a flow of fluid out of the screen. This serves to dislodge some of the debris that has become lodged in the screen 16 and urge it downwardly toward the bottom opening 20. The bypass port 26 also provides an additional flow path when the fluid becomes more viscous from low temperatures. As viscosity increases the amount of back pressure on the inlet line also increases because of the added difficulty of oil flowing through the screen 16. The bypass port 26 thus serves to alleviate some of the back pressure which can cause catastrophic failure of pumps having an external case drain.

A screen inspection and sensor port 27 is provided to allow visual inspection of the screen and to allow probes and sensors to be connected to the apparatus 10 for diagnostic purposes. For example, temperature or pressure sensors may be connected into this port for hydraulic system diagnosis. Similarly, oil samples may be taken through the screen inspection and sensor port 27. The screen 16 may also be visually inspected via this port to determine the extent of screen plugging.

The bottom opening 20 of the cylinder defined by the screen 16 is located above an opening extending into a debris collection chamber 28. Thus debris trapped by the screen 16 is pulled downwardly toward the debris collection chamber 28 by gravity and by the flow created by the bypass port 26. The debris collection chamber 28 is formed in a sensor housing 30. Preferably, the sensor housing 30 is cylindrical in shape. In the preferred embodiment, a debris sensor 32 is located adjacent the debris collection chamber 28 to detect the presence of the debris, i.e., both ferrous and non-ferrous metallic particles.

Figure 2:
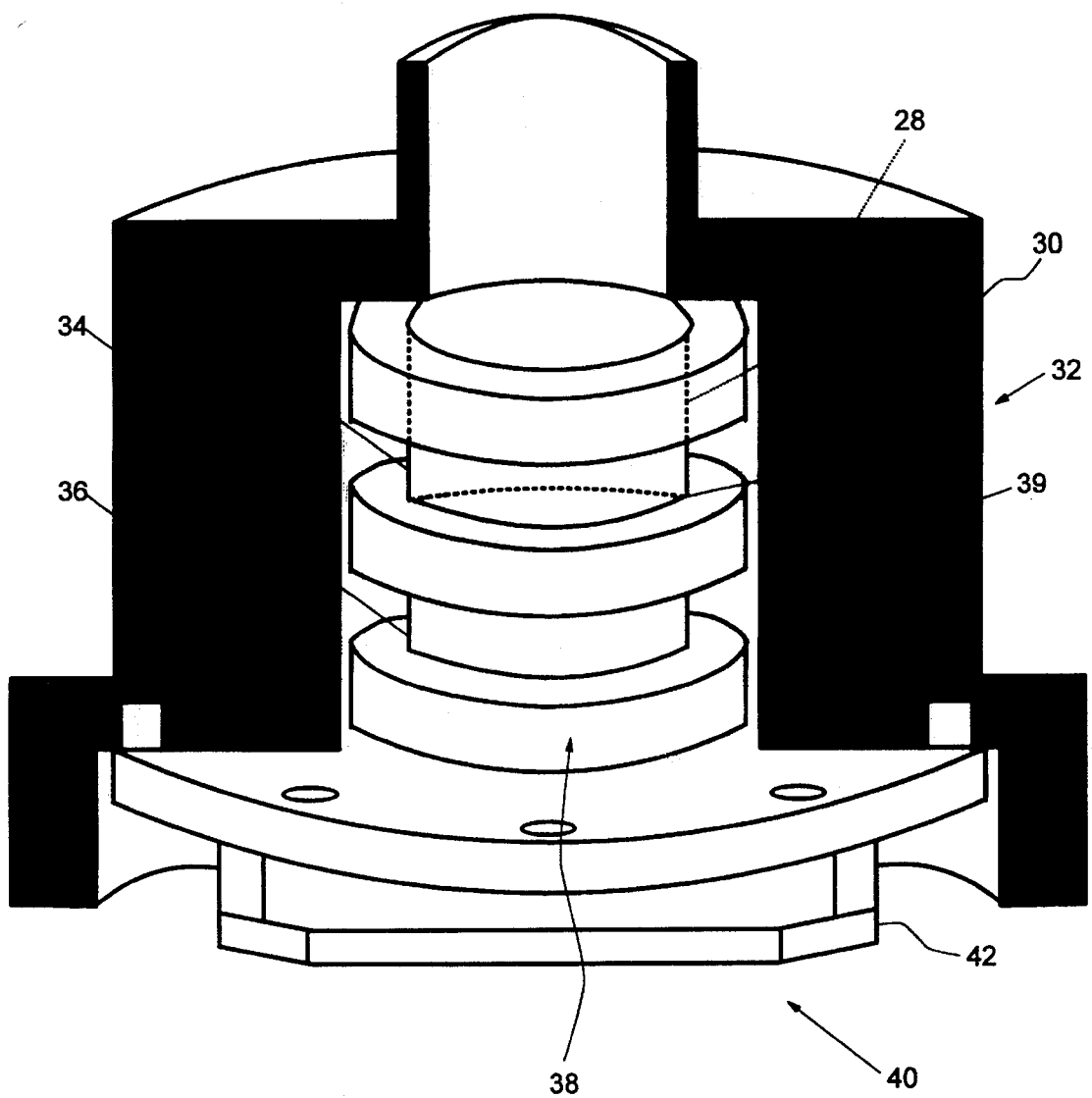
FIG. 2 is a partial, cutaway view of a debris sensing apparatus that includes two self-induction coils.

Reference is now made to FIG. 2, which shows a cross-section view of the sensor housing 30. In this view, the debris sensor 32 includes two self-induction coils 34,36 that are wound in the form of a helix about a plastic bobbin 38. The bobbin 38 defines a bore that includes the collection chamber 28. The first coil 34 is wound on the bobbin 38 about the collection chamber 28, while the reference coil 36 is wound on the bobbin 38 underneath the collection chamber 28. Note, the bottom of the collection chamber 28 is shown by reference numeral 39.

The induction of the first coil 34 is responsive to the particle accumulation within the collection chamber 28, as will be later discussed. The reference coil 36 is used to compensate for any temperature variation of the fluid. Thus, the inductance of the reference coil 36 is used as a baseline for determining the presence of particles within the cavity. In the preferred embodiment, the first and second coils 34,36 are identical and are constructed of #30 insulated wire with 200 turns.

Figure 3:
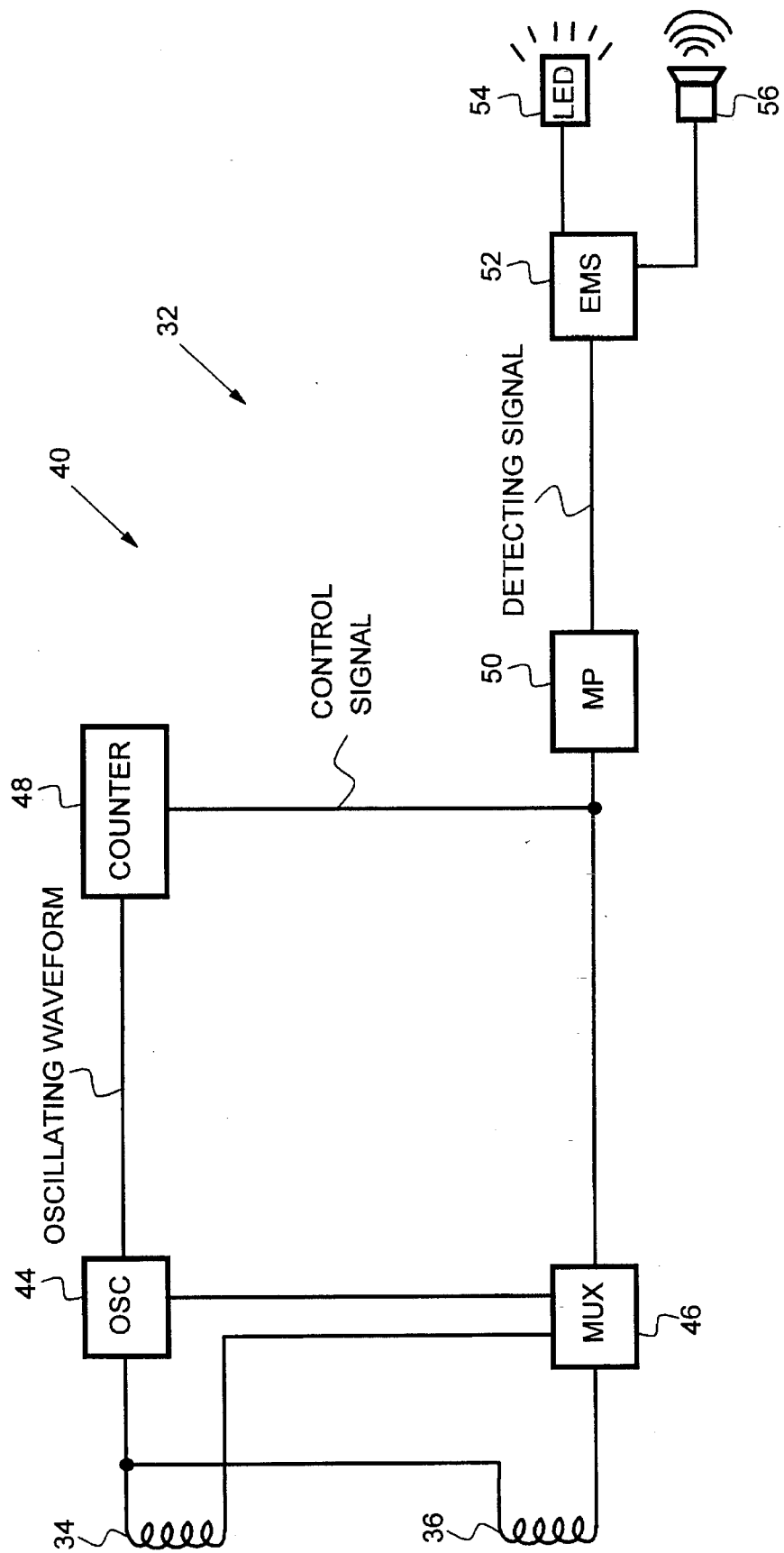
FIG. 3 is a block diagram of the electronic circuitry associated with the two-coil particle sensing apparatus.

The electronic circuitry 40 associated with the two-coil debris sensor 32 is disposed on a circuit board 42 that is located at the bottom of the housing 30. The electronic circuitry 40 is described in greater detail with reference to FIG. 3. Note, the circuit shown in FIG. 3 is exemplary, and the manner of design and construction of this, or a similar, circuit would be commonly known to a person skilled in the art.

An oscillator 44 produces an oscillating waveform. The frequency of the oscillating waveform is dependant upon a parallel resonant circuit. One such resonant circuit is formed by the first coil 34 and a capacitor (not shown), and another resonant circuit is formed by the second coil 36 (with the capacitor). A multiplexer 46 allows only one resonant circuit, i.e., coil to be energized at a given time. Preferably, the values of each resonant circuit component are chosen to cause the oscillator 44 to produce the oscillating waveform at a high frequency, e.g., approximately 300 kHz. However, as the self-inductance of the coils 34,36 change, so does the frequency of the oscillating waveform.

For example, when a metallic particle enters the collection chamber 28, the energized first coil 34, in accordance with well-known theory, introduces eddy currents in the particle. The eddy currents are a function, among other properties, of material conductivity. Thus, when a metallic particle enters the collection chamber 28, eddy currents in the particle cause the effective inductance of the first coil 34 to decrease. Consequently, the oscillator 44 will produce the oscillating waveform with an increased frequency. Because eddy currents are a function of material conductivity, the greater the size of a particle or the greater amount of particle accumulation, the greater the change in the oscillating waveform frequency.

Advantageously, the present invention is particularly suited to detect the presence of both ferrous and non-ferrous metallic particles. As is well known, eddy current principles apply to both ferrous and non-ferrous metallic particles. Further, because the first coil 34 is being energized at such a high frequency, the eddy current inductive effects are dominant over any ferromagnetic inductive effects that are caused by an increase in permeability of the first coil's magnetic circuit due to the accumulation of ferrous magnetic particles. Consequently, the change in frequency of the oscillating waveform is due to the eddy current inductive effects on both the ferrous and nonferrous particles.

Figure 4:
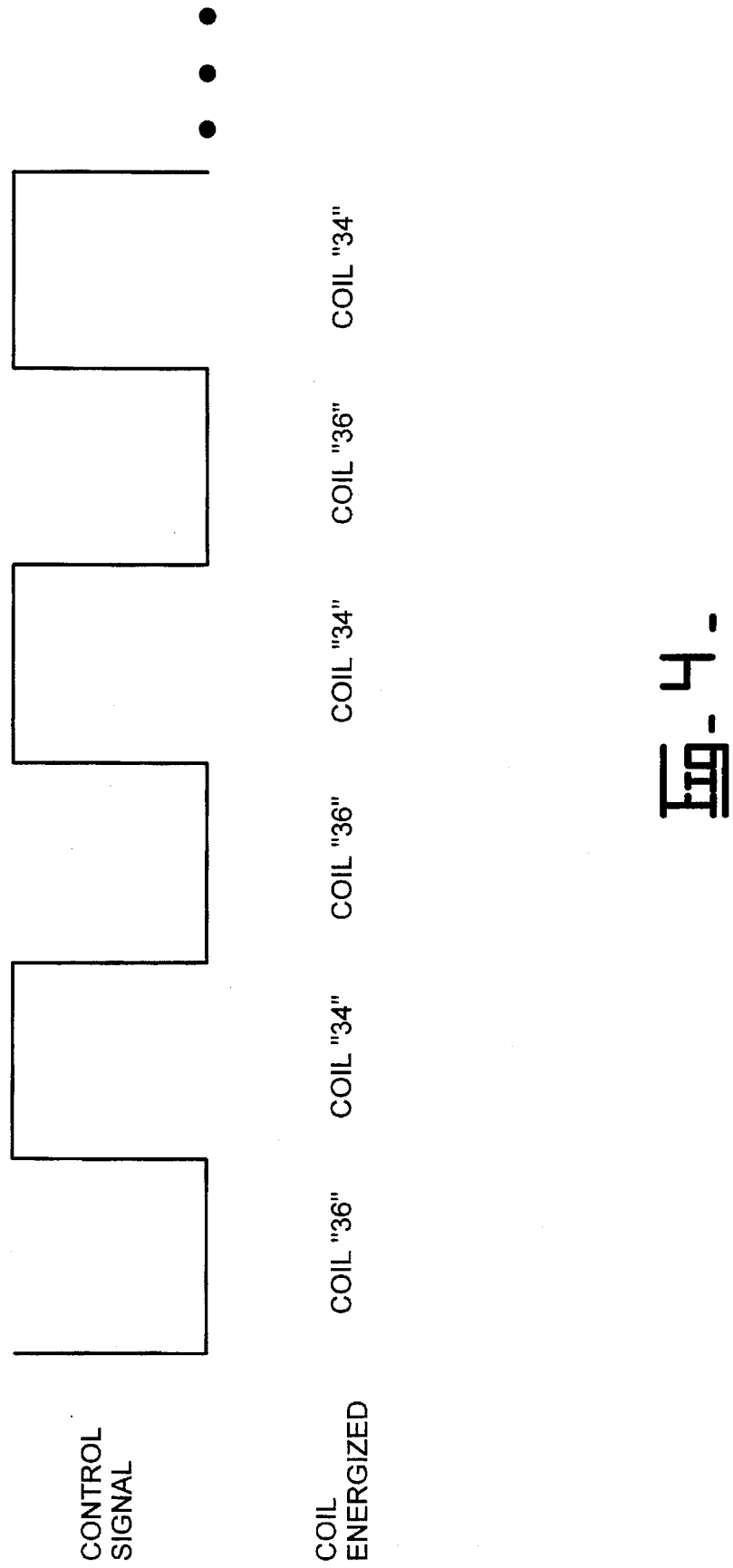
FIG. 4 is a timing diagram of a control signal associated with the electronic circuitry.

A counter 48 tallies the number of pulses associated with the oscillating waveform and responsively produces a control signal. The control signal controls the energization of the coils 34,36, as well as, provides information relating to the amount of particle accumulation in the collection chamber 28. For example, the control signal causes the multiplexer to select one coil to begin energization, while the counter 48 tallies the number of pulses associated with the oscillating waveform. Once the number of pulses reaches a predetermined number, the counter 48 changes the "state" of the control signal, which causes the multiplexer 46 to select the other coil to begin energization. Accordingly, the counter 48 tallies the number of pulses of the oscillating waveform associated with the other coil. Note, this sequence may be better shown by the timing diagram of FIG. 4.

The control signal is a continuous pulse-width-modulated signal wherein the duration of the "high" pulse level is responsive to one coil being energized, e.g., the first coil 34, while the duration of the "low" pulse level is responsive to the other coil being energized, e.g., the reference coil 36. Thus, the "high" pulse level is responsive to the frequency of the first coil 34, which is indicative of the amount of accumulation of the metallic particles (and fluid temperature); while the "low" pulse level is responsive the frequency of the reference coil 36, which is indicative of the fluid temperature only.

The microprocessor 50 receives the control signal, determines the duty cycle of the control signal, and produces a detecting signal having a pulse width modulated waveform that is indicative of the particle accumulation in the collection chamber 28.

As shown in FIG. 3, the microprocessor delivers the detecting signal to an electronic monitoring system 52. The electronic monitoring system 52 provides a warning signal to the vehicle operator in response to the duty cycle of the detecting signal being above a predetermined value. The electronic monitoring system 52 may include an LED 54 to provide a visual warning signal and/or a horn 56 to provide an audio warning signal. For example, a warning signal may be provided in response to the detecting signal being greater than a predetermined value. Further, the microprocessor 50 is able to determine the rate of particle accumulation (trending). The trending data may be accessed by a service tool of a type well-known in the art for downloading diagnostic and prognostic information. Similarly, the trending data may be sent to a remote location via a RF communication link known in the art.

In another embodiment of the present invention, the two-coil debris sensor 32 may be used to detect the total accumulation of the ferrous and non-ferrous metallic particles, the total accumulation of the ferrous particles only, and the total accumulation of the non-ferrous particles only. Advantageously, the oscillator 44 may be configured in such a manner as to produce the oscillating waveform at two different frequencies—a high frequency and a low frequency. For example, an electronic switch may be provided to increase the capacitance of the resonant circuits. Thus, in one setting, the resonant circuits are configured to cause the oscillating waveform to be produced at a high frequency, e.g., 300 kHz; and, in another setting, the resonant circuits are configured to cause the oscillating waveform to be produced at a low frequency, e.g., 30 kHz. As those well skilled in the art can appreciate, the low frequency setting may be produced by increasing the capacitance of the resonant circuits. One way to increase the capacitance of the resonant circuits is by adding a capacitor in parallel with the existing capacitor. Consequently, the electronic switch may simply "drop" the added capacitor "in" or "out" of the circuit.

The result of the high frequency oscillations is that as described above. However, the low frequency oscillations causes a different phenomena to result. For example, when a ferrous particle enters the collection chamber 28, the inductance of the energized first coil 34 increases due to the increased permeability of its magnetic circuit. The oscillator 44 therefore produces an oscillating waveform at a reduced frequency due to the increased inductance. Note, as can be appreciated by those well skilled in the art, the ferromagnetic inductive effects are dominant over any eddy current inductive effects due to the first coil 34 being energized at such a low frequency.

Thus, by producing the oscillating waveform at a high frequency, the microprocessor 50 can determine the total particle accumulation of both the ferrous and non-ferrous particles. Alternatively, by producing the oscillating waveform at a low frequency, the microprocessor 50 can determine the accumulation of the ferrous particles only. Therefore, the microprocessor 50 need only subtract the amount of the ferrous accumulation from that of the total particle accumulation in order to determine the amount of the non-ferrous particle accumulation.

Thus, while the present invention has been particularly shown and described with reference to the preferred embodiment above, it will be understood by those skilled in the art that various additional embodiments may be contemplated without departing from the spirit and scope of the present invention.

Industrial Applicability

In operation, the present invention is used to filter out debris from hydraulic fluid or any other type of lubricating fluid and detect the accumulation of both ferrous and non-ferrous particles. As components such as hydraulic pumps and motors wear, tiny particles of ferrous and non-ferrous particles become suspended in the fluid. If one of the components in the hydraulic system becomes excessively worn out and/or is about to fail, the amount of particles suspended in the oil increases substantially. Likewise, the amount of particles in the debris collection chamber will increase substantially.

The electrical signals provided by the debris sensor causes an indicator light to illuminate in the operator compartment indicating impending failure. Further, the debris sensor determines the extent and type of debris in the fluid, which may be used in diagnosing or predicting a failure. For example, trending data is stored in the microprocessor for later download to a service tool.

Other aspects, objects and advantages of the present invention can be obtained from a study of the drawings, the disclosure and the appended claims.

We claim:

1. An apparatus for detecting particles within a fluid, comprising:

a bobbin defining a debris collection chamber;

a first coil wound in a helix about the bobbin, said first coil wound about the debris collection chamber, wherein the induction of the first coil is responsive to the particle accumulation within the collection chamber;

a reference coil wound in a helix about the bobbing, said reference coil being wound below the collection chamber; and an oscillator coupled to the first and reference coils for selectively energizing the coils with an oscillating waveform at a high frequency and at a low frequency, wherein the induction of the reference coil is responsive to the fluid temperature, wherein the resulting frequency of the high frequency waveform is a function of the accumulation of both ferrous and non-ferrous particles and resulting frequency of the low frequency waveform is a function of the accumulation of only the ferrous particles.

2. An apparatus, as set forth in claim 1, including a multiplexer adapted to select one coil to energize at a given time.

3. An apparatus, as set forth in claim 2, wherein the oscillator produces an oscillating waveform having a series of pulses, the frequency of which is a function of the one energized coil inductance.

4. An apparatus, as set forth in claim 3, including a counter adapted to tally the number of waveform pulses associated with the one energized coil, and responsively produce a control signal, the counter changing the state of the control signal in response to tallying a predetermined number of pulses, wherein the multiplexer selects the other coil to energize in response to the state change of the control signal, and wherein the counter tallies the number of waveform pulses associated with the other energized coil.

5. An apparatus, as set forth in claim 4, wherein the control signal is a continuous pulse width modulated waveform, and wherein the duration of the control signal "high" pulse is responsive to the oscillating waveform frequency associated with the one coil and the duration of the control signal "low" pulse is responsive to the oscillating waveform frequency associated with the other coil.

6. An apparatus, as set forth in claim 5, including a microprocessor adapted to receive the control signal, determine the particle accumulation in the collection chamber in response to the duty cycle of the control signal, and produce a detecting signal having a pulse width modulated waveform indicative of the particle accumulation in the collection chamber.

7. An apparatus, as set forth in claim 6, including an electronic monitoring system adapted to receive the detecting signal and produce a warning signal in response to the detecting signal duty cycle being greater than a predetermined value.

8. An apparatus, as set forth in claim 1, including:

an inlet port;

a screen being substantially cylindrical in shape and having a pair of open ends, the inlet port and screen being disposed such that fluid entering the inlet port flows into the screen chamber through one of the open ends;

a screen chamber being substantially cylindrical in shape and of larger diameter than the screen, the screen being disposed within the screen chamber, the screen chamber being connected to the debris collection chamber; and an outlet port connected to the screen chamber.

9. An apparatus, as set forth in claim 8, including a bypass means for directing fluid flow between the inlet port and the screen chamber without flowing through one of the open ends.

10. An apparatus, as set forth in claim 8, wherein the inlet port and the screen chamber are disposed substantially at a right angle.

11. An apparatus, as set forth in claim 9, wherein the outlet port and screen chamber are disposed substantially at a right angle.

12. An apparatus, as set forth in claim 9, wherein fluid flows substantially radially outwardly through the screen and the bypass means directs fluid flow from the inlet port downwardly and radially inwardly into the screen chamber.

13. An apparatus, as set forth in claim 9, wherein fluid flows substantially radially outwardly through the screen and the bypass means directs fluid flow from the inlet port radially inwardly into the screen chamber and toward the debris collection chamber.

14. An apparatus, as set forth in claim 8, wherein the debris collection chamber is located below the screen chamber and is in fluid communication with the screen chamber whereby debris filtered out of the fluid is pulled toward the debris collection chamber by gravity.

15. An apparatus, as set forth in claim 9, wherein fluid flow from the bypass means dislodges particles from the screen and urges debris toward the debris collection chamber.

16. A method for operating an apparatus for detecting particles within a fluid, the apparatus including:

a bobbin defining a debris collection chamber;

a first coil wound in a helix about the bobbin, said first coil wound about the debris collection chamber, wherein the induction of the first coil is responsive to the particle accumulation within the collection chamber;

a reference coil wound in a helix about the bobbin, said reference coil being wound below the collection chamber; and an oscillator coupled to the first and reference coils for energizing the coils with an oscillating waveform, wherein the induction of the reference coil is responsive to the fluid temperature;

the method comprising the steps of:

producing an oscillating waveform at a high frequency for inducing eddy currents in the ferrous and nonferrous particle accumulation; and producing an oscillating waveform at a low frequency for increasing the permeability of the magnet circuits of the energized coils as a function of the ferrous particle accumulation.

17. A method, as set forth in claim 16, including the steps of:

energizing the first coil at a high frequency and determining the resulting frequency of the oscillating waveform; thereafter energizing the reference coil at a high frequency and determining the resulting frequency of the oscillating waveform; and responsively determining the amount of particle accumulation of the ferrous and non-ferrous particles in the collection chamber.

18. A method, as set forth in claim 17, including the steps of:

energizing the first coil at a low frequency and determining the resulting frequency of the oscillating waveform; thereafter energizing the reference coil at a low frequency and determining the resulting frequency of the oscillating waveform; and responsively determining the amount of particle accumulation of the ferrous particles in the collection chamber.

19. A method, as set forth in claim 18, including the steps of determining the amount of particle accumulation of the non-ferrous particles in response to subtracting the ferrous particle accumulation total from the ferrous and non-ferrous particle accumulation total.

* * * * *